United States Patent [19]
Bombardelli et al.

[11] Patent Number: 5,912,265
[45] Date of Patent: Jun. 15, 1999

[54] PHARMACEUTICAL COMPOSITIONS CONTAINING FLAVANOLIGNANES AND METHODS FOR USING SAME AS AN ANTIPROLIFERATIVE

[75] Inventors: Ezio Bombardelli; Paolo Morazzoni, both of Milan, Italy

[73] Assignee: Indena S.p.A., Milan, Italy

[21] Appl. No.: 08/952,415

[22] PCT Filed: Oct. 10, 1995

[86] PCT No.: PCT/EP95/03993

§ 371 Date: Nov. 18, 1997

§ 102(e) Date: Nov. 18, 1997

[87] PCT Pub. No.: WO96/37209

PCT Pub. Date: Nov. 28, 1996

[30]    Foreign Application Priority Data

May 23, 1995  [IT]  Italy ................................. MI95A1047

[51] Int. Cl.⁶ .......................... A61K 31/335; A61K 31/35
[52] U.S. Cl. ............................................ 514/452; 514/456
[58] Field of Search ..................... 514/452, 456

[56]    References Cited

FOREIGN PATENT DOCUMENTS 2 261 434    5/1993    United Kingdom .

OTHER PUBLICATIONS

Mai et al., Zhonghua Xinxueguanbing Zazhi, 15(1), 49–51, Abstract only, 1987.
Pietrangelo et al., Gastroenterology, 109(6), 1941–9 Abstract only, 1995.
V. Steele et al., "Preclinical Efficacy Evaluation of Potential Chemopreventive Agents in Animal Carcinogenesis Models: Methods and Results From the NCI Chemoprevention Drug Development Program," *Journal of Cellular Biochemistry*, Supplement 20:32–54 (1994).
Abstract No. 95–215777, "Capsule For Curing Hepatitis," Derwent Publications Ltd., p. 1, Apr. 27, 1994.
R. Invernizzi, et al., "Silymarine During Maintenance Therapy of Acute Promyelocytic Leukemia," *Haematologica*, Letters to the Editor, 78:340–341 (1993).
V. Steele et al., "Inhibition of Transformation in Cultured Rat Tracheal Epithelial Cells by Potential Chemopreventive Agents," *Cancer Research*, 50:2068–2074 (Apr. 1, 1990).

*Primary Examiner*—Jerome D. Goldberg
*Attorney, Agent, or Firm*—Pennie & Edmonds LLP

[57]    ABSTRACT

The invention relates to methods for preventing, inhibiting, or suppressing tumors by administering to a person in need of such treatment a therapeutically effective amount of one or more flavanolignanes, such as silymarin, silybin, silidianin, silicristin, dehydrosilybin, mixtures thereof, or extracts thereof as an antiproliferative. The invention further relates to the antitumor pharmaceutical composition includes a therapeutically effective amount of the flavanolignane selected from the group of silymarin, silybin, silidianin, silicristin, dehydrosilybin, and mixtures thereof, in combination with a different antitumor agent. In another embodiment, the pharmaceutical composition includes a therapeutically effective amount of a flavanolignane selected from the group of silidianin, silicristin, and mixtures thereof, with a pharmaceutically acceptable carrier or excipient. The compositions and method may be prepared or administered with different antitumoral agents for concurrent or sequential use for treating tumors, such as those typically found in the uterus, ovary, and breast.

6 Claims, 1 Drawing Sheet

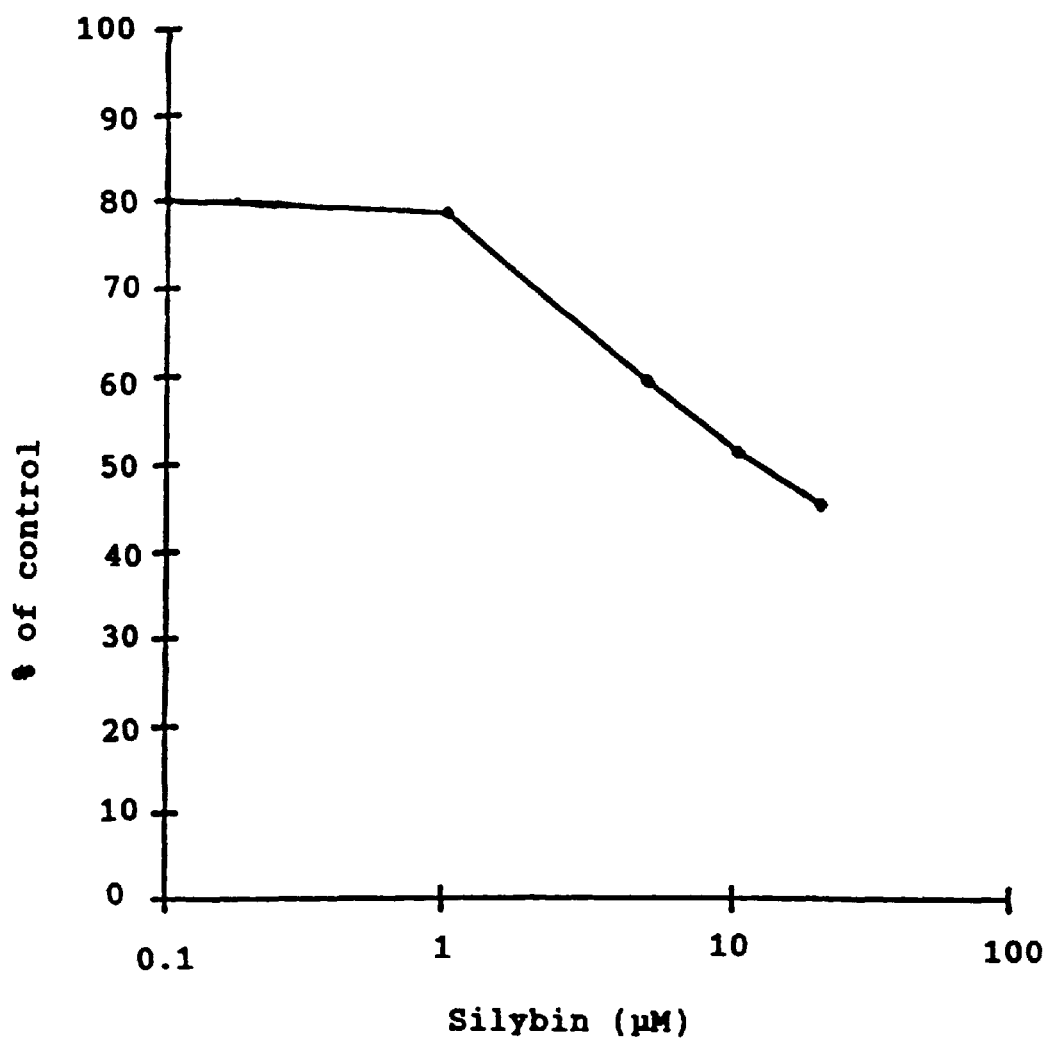
Figure 1  Inhibition curve of the growth of A2780 WT treated with silybin

PHARMACEUTICAL COMPOSITIONS CONTAINING FLAVANOLIGNANES AND METHODS FOR USING SAME AS AN ANTIPROLIFERATIVE

This application is a 371 of PCT/EP95/03993 filed Oct. 10, 1995.

FIELD OF THE INVENTION

The present invention relates to the use of flavanolignanes, alone or combined with known chemotherapeutic agents, for the preparation of medicaments for the therapy and prophylaxis of uterus, ovary and breast tumors.

BACKGROUND OF THE INVENTION

Recently, some flavonoids have been found to have antitumoral activity (Verna, Cancer Research 48, 5754, 1988) and chemoprophylactic activity in some tumors (Cassady, J. Nat. Prod. 53, 23, 1990). Particularly quercetin, a flavonoid which is almost ubiquitous in plants, has proved some inhibiting activity on the proliferation of human leukemia cells (Larocca, Br. J. of Haematology 75, 489, 1990) and on other cell lines (Scambia, Br. J. Cancer 62, 942, 1990—Int. J. Cancer 46, 1112, 1990—Cancer Chemother. Pharmacol. 28, 255, 1991—Gynecologic Oncology 45, 13, 1992) besides having a synergistic activity with the usual chemotherapeuticals. Though the mechanism of such an inhibiting action on proliferation is unknown, it seems to be connected with the interaction of this flavonoid with the estrogen receptors of type II (Markaverich, J. steroid Biochem. 30, 71, 1988). These receptors, first described by Clark (J. Biol. Chem. 253, 7630, 1978) in the rat uterus, are different from the real estrogen receptors (ER) since these are present in a higher concentration and have a dissociation affinity constant ($K_D$: 10–20 nM) for estradiol lower than that of the estrogen receptors ($K_D$: 0.2–1 nM).

SUMMARY OF THE INVENTION

The invention relates to methods for preventing, inhibiting, or suppressing tumors by administering to a person in need of such treatment a therapeutically effective amount of a flavanolignane selected from the group of silymarin,, silybin, silidianin, silicristin, dehydrosilybin, and mixtures thereof. The flavanolignane exhibits antagonistic activity on type II estrogen receptors and antiproliferative activity. In one embodiment, the flavanolignane is provided in a concentration from 0.01 $\mu$M to 20 $\mu$M. In a preferred embodiment, the flavanolignane is provided in an amount from 50 to 1,500 mg/day.

In a preferred embodiment, the method also includes administering a therapeutically amount of a different antitumor agent with the flavanolignane. In a more preferred embodiment, the different antitumor agent is administered concurrently or sequentially with the flavanolignane. In another preferred embodiment, the different antitumor agent includes cisplatin or adriamycin.

In one embodiment, the flavanolignane is administered together with a pharmaceutically acceptable carrier or excipient. In a preferred embodiment, the carrier or excipient includes a glyceride or a phospholipid. In a more preferred embodiment, the glyceride includes a liquid semi-synthetic glyceride of one or more medium-chain fatty acids. In a different embodiment, the administration is selected to be oral.

The invention also relates to antitumor pharmaceutical compositions including a therapeutically effective amount of a flavanolignane selected from the group of silymarin, silybin, silidianin, silicristin, dehydrosilybin, and mixtures thereof, in combination with a different antitumor agent. In one embodiment, the flavanolignane is present in a concentration from 0.01 $\mu$M to 20 $\mu$M. In a preferred embodiment, the composition includes an amount from 50 to 1,500 mg/day of the flavanolignane.

In a preferred embodiment, the different antitumor agent is concurrently administered with the flavanolignane. In a more preferred embodiment, the different antitumor agent includes cisplatin or adriamycin.

In another embodiment, the composition includes a pharmaceutically acceptable carrier or excipient. In a preferred embodiment, the carrier includes a phospholipid or a liquid semi-synthetic glyceride of one or more medium-chain fatty acids. In a different embodiment, the composition is suitable for oral administration.

The invention also relates to a pharmaceutical composition includes a therapeutically effective amount of a flavanolignane selected from the group of silidianin, silicristin, and mixtures thereof, with a pharmaceutically acceptable carrier or excipient.

Now it has surprisingly been found that flavanolignanes, among which silymarin, already widely used in therapy for the treatment of hepatopathias of various origin, the three main components thereof being known under the names silybin, silidianin, silicristin and dehydrosilybin and having the structures reported below:

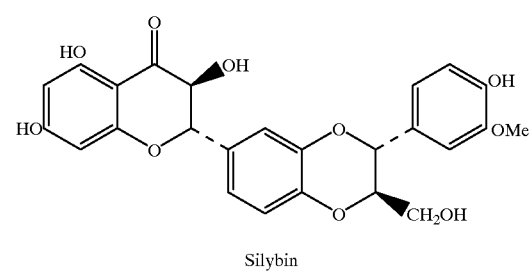

Silybin

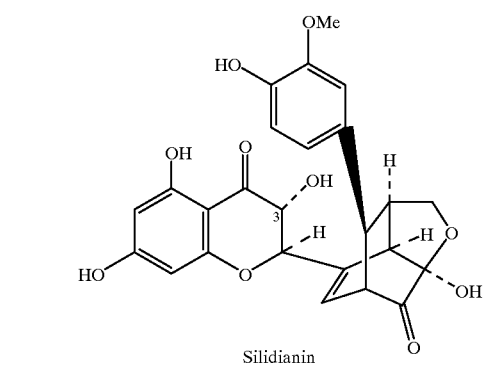

Silidianin

-continued

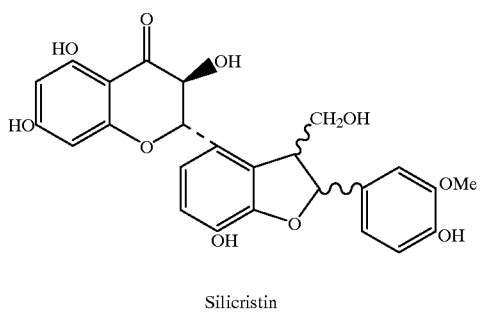

Silicristin have a high affinity to the estrogen receptors of type II and a very marked antiproliferative activity on uterus, ovary and breast tumoral cell lines resistant to Cis-platin and adriamycin. In order to verify the antiproliferative effect of flavanolignanes, the growth curves of different stabilized cell lines deriving from various human tumors have been examined in the presence of the compounds and their capability to interact with the Type II EBS in ovary carcinoma samples has been evaluated.

The determination of the binding to the estrogen receptor has been carried out on cells of ovary tumor or of other organ tumors, cultured in monolayers using as medium the Dulbecco Modified Medium added with calf serum and with 200 unities/ml of penicillin. The cells used for the tests have been trypsinated every week and

DETAILED DESCRIPTION OF THE INVENTION placed on a plate at a $8 \times 10^{-4}$/ml density and incubated at 37° C. under air atmosphere containing 5% $CO_2$ and humidity. For the control of the antiproliferative activity of the products, the cells have been placed into wells (Falcon 3046, Becton Dickinson N.Y.) at a concentration of $4 \times 10^4$/ml. After 24 hours the medium is substituted with fresh medium and the flavanolignanes dissolved in absolute ethanol are added. The controls are treated in the same experimental conditions only with the vehicle in the absence of the active ingredient. The treatment described above is repeated at 24 hour intervals during the 72 hours of the test time. The inhibition of the cell proliferation is evaluated by direct count of the cells, comparing the growth of the controls versus that of the treated samples.

For the dosage of the receptors, the cells after 24 hours are incubated with scalar amounts of labeled estradiol ($^3$H-E2 40Ci/mmol, Amershan UK) alone or in the presence of a 100-fold amount of diethylstilbestrol at 4° C. for 2.5 hours.

At the end of the incubation time, the cells are quickly washed with fresh substrate and incubated for 30 minutes with 1M NaOH. Radioactivity is measured by means of a scintiller and binding specificity is calculated from the difference between the preparations containing or not diethylstilbestrol. Results are expressed as the number of binding sites per cell, according to conventional methods of the literature (Raneletti, 1988).

The inhibition on cell proliferation is evaluated by direct count of the cells, comparing the growth of controls versus that of the treated ones.

The results on different cell lines are reported in FIG. 1 and in Tables I and V.

DETAILED DESCRIPTION OF DRAWING

In particular, FIG. 1 shows the antiproliferative activity of silybin on A2780 WT, an ovary carcinoma cell line ER negative, type II positive.

The results are the average of two experiments carried out in triplicated. Standard deviations are less than 10%.

The antiproliferative activity is dose-dependent.

Table I reports the data relating silybin used at concentrations from 0.01 $\mu$M to 20 $\mu$M in cell proliferation; silybin exerts a dose-dependent antiproliferative effect on the different cell lines, including those resistant to chemotherapeuticals (MCF-7 ADRr, A2780 CIS) with a $IC_{50}$ from 4.8 to 24 $\mu$M.

TABLE I

Silybin antiproliferative effect on different stabilized cell lines

| CELL LINES | TEST* NUMBER | CELL TYPE | EXPOSURE TIME | $IC_{50}$ $\mu$M |
|---|---|---|---|---|
| A2780 WT | 8 | ovary ca | 72 h | 12 |
| A2780 CIS | 5 | ovary ca CIS resistant | 72 h | 14 |
| OVCA-433 | 3 | ovary ca | 72 h | 4.8 |
| MCF-7 ADRr | 5 | breast ca ADR resistant | 72 h | 24 |

*each test was carried out in triplicated.

In order to further study the antiproliferative activity of silybin, the effect of this substance on A2780 WT cell cycle has been studied. As shown in Table II, cytofluorimetric analysis reveals that silybin causes a decrease in the percentage of phase S cells and a mild increase in those in phase G0/G1.

TABLE II

Effect of silybin on the distribution of A2780 WT in different phases of the cell cycle.

| | TREATMENT* | |
|---|---|---|
| | Control | Silybin (10 $\mu$M) |
| G0/G1 | 58.7** | 70.5 |
| S | 31 | 20.9 |
| G2/M | 10.3 | 8.6 |

*A2780 WT cells were cultured for 2 days with or without 10 $\mu$M silybin.
**Results are expressed as the cell percentage in each phase of the cell cycle.

On the basis of these results, silybin was tested for any enhancement on the effect of some chemotherapeuticals, particularly cisplatin (CIS) and adriamycin (ADR). As reported in Table III, when silybin is used in combination with CIS, a synergistic inhibition effect on the growth is observed, compared with corresponding doses of the medicaments used alone.

Similar results are obtained using silybin in combination with ADR (Tab. IV).

In order to verify wether such an effect of a combination of silybin with adriamycin or cisplatin is due to a synergistic or an additive action, the data have been analyzed with the isobolic method by Berenbau (Adv. Cancer Res., 25, 269, 1981). The resulting combination index was less than 1 in both parental (A2780 WT, Tab. III) and resistant (MCF7, ADRr, Tab. IV) cell lines, thus proving that the combination of the two medicaments exerts a synergistic antiproliferative activity.

TABLE III

Synergistic antiproliferative effect of the CIS-silybin combination on A2780 WT cell line.

| CIS (μg/ml) | Silybin (μM) | % control | CIS (μg/ml) | Silybin (μM) | Combination index |
|---|---|---|---|---|---|
| 0.1 | 0.1 | 67 | 0.23 | 2.9 | 0.46 |
| 0.25 | 0.1 | 58 | 0.31 | 6.4 | 0.81 |
| 0.5 | 0.1 | 37 | 0.54 | >50 | <0.92 |
| 1 | 0.1 | 18 | >1 | >50 | <1.00 |
| 0.1 | 1 | 54 | 0.34 | 8.2 | 0.41 |
| 0.25 | 1 | 35 | 0.56 | >50 | <0.46 |
| 0.5 | 1 | 25 | 0.82 | >50 | <0.62 |
| 1 | 1 | 12 | >1 | >50 | <1.02 |

TABLE IV

Synergistic antiproliferative effect of a combination of ADR and silybin on MCF-7 ADRr line.

| ADR (μg/ml) | Silybin (μM) | % control | ADR (μg/ml) | Silybin (μM) | Combination index |
|---|---|---|---|---|---|
| 0.1 | 0.1 | 80 | 0.6 | 0.1 | 1.16 |
| 0.5 | 0.1 | 76 | 0.9 | 0.36 | 0.77 |
| 1 | 0.1 | 69 | 2.5 | 2.2 | 0.44 |
| 2.5 | 0.1 | 62 | 5.4 | 7 | 0.51 |
| 5 | 0.1 | 47 | >10 | 35 | <0.50 |
| 10 | 0.1 | 39 | >10 | >50 | <1.00 |

The antiproliferative activity of silybin and its analogous is observed not only on stabilized cell lines but also on human tumor primary cultures. A plurality of the tested flavanolignanes have a similar behaviour. In Table V, the data relating to silybin, silidianin, silymarin and dehydrosilybin are reported. The diastereomeric forms of silybin and isosilybin are as well active in these tests.

TABLE V

Effect of different flavanolignanes on the growth of A2780 WT cells.

| COMPOUND | TEST NUMBER | EXPOSURE TIME | $IC_{50}$ μM |
|---|---|---|---|
| SILYBIN | 8 | 72 h | 12 |
| DEHYDROSILYBIN | 3 | 72 h | 2.88 |
| SILIDIANIN | 3 | 72 h | 12 |
| SILYMARIN | 3 | 72 h | 15 |

Moreover, the above flavanolignanes were evidenced to inhibit in vivo the cell proliferation, by measuring the size of tumors implanted in the nude athymic mouse according to the conventional conditions of literature. The treatment of the animals at doses from 1 to 100 mg/Kg evidenced a marked regression of the studied tumors until their disappearance in a high percentage of individuals. The products in man proved to have an activity in ovary, breast and uterus tumors higher than that of known medicaments, such as Tamoxifen.

Silidianin, dehydrosilybin and the two diastereomeric forms of silybin showed a particularly marked activity. In the in vitro tests flavanolignanes have been used as such, whereas in in vivo tests the complexes thereof with phospholipids, described in EP-A-0209038, have been used.

According to the invention, flavanolignanes can be administered orally or by infusion: for the oral route, natural or synthetic phospholipids proved to be particularly useful as carriers, since they form the above cited liposoluble stable complexes with said compounds; as well as liquid semi-synthetic glycerides containing medium-chain fatty acid triglycerides or analogues which can enhance the bioavailability of the single compounds, of the natural mixtures thereof or of the extracts containing them.

The flavanolignanes dosage in man range from 50 to 1500 mg/day, mainly administered by the oral route.

The invention also relates to compositions containing silymarin flavanolignanes and an antitumoral agent in the form of combinations for the simultaneous, sequential or separated use, in the antitumoral therapy.

The following examples further illustrate the invention.

EXAMPLES

Example 1

Hard gelatin capsules containing the complex of silybin with soy phosphatidylcholine.

Composition:

| | |
|---|---|
| silybin-soy phosphatidylcholine complex | 300 mg |
| sodium carboxymethylcellulose | 16 mg |
| talc | 6 mg |
| magnesium stearate | 3 mg |

Example 2

Soft gelatin capsules containing dehydrosilybin.

Composition:

| | |
|---|---|
| dehydrosilybin | 250 mg |
| liquid semi-synthetic glycerides | 300 mg |
| partially hydrogenated vegetable oils | 49 mg |
| soy lecithin | 1 mg |

Example 3

Hard gelatin capsules containing the complex of silymarin with soy natural phospholipids.

Composition:

| | |
|---|---|
| silymarin-soy natural phospholipids complex | 360 mg |
| sodium carboxymethylcellulose | 21 mg |
| talc | 6 mg |
| magnesium stearate | 3 mg |

Example 4

Hard gelatin capsules containing the complex of silidianin with soy phosphatidylcholine.

Composition:

| | |
|---|---|
| silidianin-soy phosphatidylcholine complex | 200 mg |
| sodium carboxymethylcellulose | 10 mg |
| talc | 3 mg |
| magnesium stearate | 2 mg |

What is claimed is:

1. A method for preventing, inhibiting or suppressing estrogen dependent tumors sensitive to the flavanolignane below which comprises administering to a person in need of such treatment a therapeutically effective amount of flavanolignane selected from the group consisting of silymarin, silybin, silidianin, silicristin, dehydrosilybin, a phospholipid complex of one of these flavanolignanes, and mixtures thereof, wherein the administration is orally or by infusion.

2. The method of claim 1, wherein the flavanolignane is provided in an amount from 50 to 1,500 mg/day.

3. The method of claim 1, wherein the flavanolignane is administered with a pharmaceutically acceptable carrier or excipient.

4. The method of claim 3, wherein the carrier or excipient comprises a glyceride or a phospholipid.

5. The method of claim 4, wherein the glyceride is selected to include a liquid semi-synthetic glyceride of one or more medium-chain fatty acids.

6. A method for preventing, inhibiting or suppressing uterus, ovary and breast tumors which comprises administering to a person in need of such treatment a therapeutically effective amount of flavanolignane selected from the group consisting of silymarin, silybin, silidianin, silicristin, dehydrosilybin, a phospholipid complex of one of these flavanolignanes, and mixtures thereof, wherein the administration is orally or by infusion.

* * * * *